(12) United States Patent
Fukai et al.

(10) Patent No.: US 6,274,704 B1
(45) Date of Patent: Aug. 14, 2001

(54) PEPTIDES DERIVED FROM THE HEPARIN BINDING DOMAIN OF FIBRONECTIN

(75) Inventors: Fumio Fukai, Tokorozawa; Takashi Katayama, Shinjuku-ku, both of (JP)

(73) Assignee: Hisamitsu Pharmaceutical Co., Inc., Tosu (JP)

( * ) Notice: Subject to any disclaimer, the term of this patent is extended or adjusted under 35 U.S.C. 154(b) by 0 days.

(21) Appl. No.: 08/933,100

(22) Filed: Sep. 18, 1997

(30) Foreign Application Priority Data

Sep. 19, 1996 (JP) .................................................. 8-248247

(51) Int. Cl.$^7$ .......................... C07K 14/78; C07K 14/00; C07K 7/06; C07K 7/08
(52) U.S. Cl. .......................... 530/326; 530/300; 530/317; 530/328; 530/350; 530/353
(58) Field of Search .................................. 514/2, 8, 885; 530/300, 327, 325, 329, 350

(56) References Cited

U.S. PATENT DOCUMENTS 5,019,646   5/1991   Furcht et al. .

FOREIGN PATENT DOCUMENTS

WO 94/13692   6/1994   (WO) .

OTHER PUBLICATIONS

Fukai, et al., "Identification of the Anti–Adhesive Site Buried within the Heparin–Binding Domain of Fibronectin", J. Biochem. 121 (1997), pp. 189–192.

Yamada et al, "Fibronectins—Adhesive Glycoproteins of Cell Surface and Blood", Nature, vol. 275, Sep. 21, 1978, pp. 179–184.

Plantefaber et al, "Changes in Integrin Receptors on Oncogneically Transformed Cells", Cell, vol. 56, Jan. 27, 1989, pp. 281–290.

McCarthy et al, "Laminin and Fibronectin Promote the Haptotactic Migration of B16 Mouse Melanoma Cells In Vitro", The Journal of Cell Biology, vol. 98, Apr. 1984, pp. 1474–1480.

Pierschbacher et al, "Cell Attachment Activity of Fibronectin Can be Duplicated by Small Synthetic Fragments of the Molecule", Nature, vol. 309, May 3, 1984, pp. 30–33.

Pytela et al, "Identification and Isolation of a 140 kd Cell Surface Glycoprotein with Properties Expected of a Fibronectin Receptor", Cell, vol. 40, Jan. 1985, pp. 191–198.

Humphries et al, "A Synthetic Peptide From Fibronectin Inhibits Experimental Metastasis of Murine Melanoma Cells", Science, vol. 233, Jul. 25, 1986, pp. 467–470.

Sakai et al, "Antimetastatic Activity of Polymeric RGDT Peptides Conjugated With Poly(ethylene glycol)", JPN. J. Cancer Res., vol. 84, 1993, pp. 558–565.

Hynes et al, "Fibronectins: Multifunctional Modular Glycoproteins", The Journal of Cell Biology, vol. 95, Nov. 1982, pp. 369–377.

Fukai et al, "Fibronectin Harbors Anticell Adhesive Activity", Biochemical and Biophysical Research Communications, vol. 220, (1996), pp. 394–398.

Komazawa et al, "Synthetic Arg–Gly–Asp–Ser Analogues of the Cell Recognition Sites of Fibronectin That Retain Antimetastatic and Anti–Cell Adhesive Properties", Biol. Pharm. Bull., vol. 16, No. 10 (1993), pp. 997–1003.

Miekka et al, "Rapid Methods for Isolation of Human Plasma Fibronectin", Thrombosis Research, vol. 27, 1982, pp. 1–14.

Hynes, "Integrins: A Family of Cell Surface Receptors", Cell, vol. 48, Feb. 27, 1987, pp. 549–554.

Yoneda et al. Exptl. Cell Res. 217: 169–179 (1995).*

Cell Structure and Function 21(6):682 (1996).*

* cited by examiner

*Primary Examiner*—Phillip Gambel
(74) *Attorney, Agent, or Firm*—Pillsbury Madison & Sutro, LLP

(57) ABSTRACT

The biologically active peptide of the invention has a number of amino acids of 30 or less, comprises an amino acid sequence described as SEQ ID NO:13 (Tyr Thr Ile Tyr Val Ile Ala Leu) in the sequence listing and has cell adhesion inhibition activity. The peptide of the invention has short length and, therefore, synthesis and handling of the peptide are easy.

4 Claims, 3 Drawing Sheets

III14-2A

III14-2

III14-2B

III14-2C

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 31 amino acids (B) TYPE: amino acid
            (C) STRANDEDNESS: single
            (D) TOPOLOGY: linear (ii) MOLECULE TYPE: peptide (ix) FEATURE:
            (D) OTHER INFORMATION: Sequence of a part (1600-1630) of
                Heparin binding site of human plasma fibronectin (xi) SEQUENCE DESCRIPTION: SEQ ID NO:1:

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly
                20                  25                  30

(2) INFORMATION FOR SEQ ID NO:2:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: Sequence of a part (1647-1668) of
                Heparin binding site of human plasma fibronectin (xi) SEQUENCE DESCRIPTION: SEQ ID NO:2:

Ile Asn Leu Ala Pro Asp Ser Ser Ser Val Val Val Ser Gly Leu Met
 1               5                  10                  15

Val Ala Thr Lys Trp Glu
                20

(2) INFORMATION FOR SEQ ID NO:3:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: Sequence of a part (1669-1691) of
                Heparin binding site of human plasma fibronectin (xi) SEQUENCE DESCRIPTION: SEQ ID NO:3:

Val Ser Val Tyr Ala Leu Lys Asp Thr Leu Thr Ser Arg Pro Ala Gln
 1               5                  10                  15

Gly Val Val Thr Thr Leu Glu
                20

(2) INFORMATION FOR SEQ ID NO:4:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: Sequence of a part (1692-1720) of
                Heparin binding site of human plasma fibronectin

```
   (xi) SEQUENCE DESCRIPTION: SEQ ID NO:4:

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile
            20                  25

(2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:  Sequence of a part (1721-1745) of
            Heparin binding site of human plasma fibronectin (xi) SEQUENCE DESCRIPTION: SEQ ID NO:5:

Thr Gly Phe Gln Val Asp Ala Val Pro Ala Asn Gly Gln Thr Pro Ile
 1               5                  10                  15

Gln Arg Thr Ile Lys Pro Asp Val Arg
            20                  25

(2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1746-1770) of
            Heparin binding site of human plasma fibronectin (xi) SEQUENCE DESCRIPTION: SEQ ID NO:6:

Ser Tyr Thr Ile Thr Gly Leu Gln Pro Gly Thr Asp Tyr Lys Ile Tyr
 1               5                  10                  15

Leu Tyr Thr Leu Asn Asp Asn Ala Arg
            20                  25

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1787-1815) of
            Heparin binding site of human plasma fibronectin (xi) SEQUENCE DESCRIPTION: SEQ ID NO:7:

Asn Leu Arg Phe Leu Ala Thr Thr Pro Asn Ser Leu Leu Val Ser Trp
 1               5                  10                  15

Gln Pro Pro Arg Ala Arg Ile Thr Gly Tyr Ile Ile Lys
            20                  25

(2) INFORMATION FOR SEQ ID NO:8:
```

```
    (i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1835-1855) of
            Heparin binding site of human plasma fibronectin (xi) SEQUENCE DESCRIPTION: SEQ ID NO:8:

Thr Glu Ala Thr Ile Thr Gly Leu Glu Pro Gly Thr Glu Tyr Thr Ile
1               5                   10                  15

Tyr Val Ile Ala Leu
            20

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of cell binding site of human
            plasma fibronectin (xi) SEQUENCE DESCRIPTION: SEQ ID NO:9:

Gly Arg Glu Asp Ser Pro
1               5

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1829-1841) of
            Heparin binding site of human plasma fibronectin (xi) SEQUENCE DESCRIPTION: SEQ ID NO:10:

Arg Pro Arg Pro Gly Val Thr Glu Ala Thr Ile Thr Gly
1               5                   10

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1842-1860) of
            Heparin binding site of human plasma fibronectin (xi) SEQUENCE DESCRIPTION: SEQ ID NO:11:

Leu Glu Pro Gly Thr Glu Tyr Thr Ile Tyr Val Ile Ala Leu Lys Asn
```

-continued

```
                1               5              10              15
Asn Gln Lys
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1848-1860) of
            Heparin binding site of human plasma fibronectin (xi) SEQUENCE DESCRIPTION: SEQ ID NO:12:

```
Tyr Thr Ile Tyr Val Ile Ala Leu Lys Asn Asn Gln Lys
 1               5                      10
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Sequence of a part (1848-1855) of
            Heparin binding site of human plasma fibronectin (xi) SEQUENCE DESCRIPTION: SEQ ID NO:13:

```
Tyr Thr Ile Tyr Val Ile Ala Leu
 1               5
```

(2) INFORMATION FOR SEQ ID NO:14:

(i) SEQUENCE CHARACTERISTICS:
        (A) LENGTH: 271
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: sequence of a part (1600-1870) of
            Heparin binding site of human plasma fibronectin (xi) SEQUENCE DESCRIPTION: SEQ ID NO:14:

```
Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
                20                  25                  30

Arg Val Arg Val Thr Pro Lys Glu Lys Thr Gly Pro Met Lys Glu Ile
             35                  40                  45

Asn Leu Ala Pro Asp Ser Ser Ser Val Val Ser Gly Leu Met Val
         50                  55                  60

Ala Thr Lys Trp Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                 85                  90                  95
```

```
Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
            115                 120                 125

Val Pro Ala Asn Gly Gln Thr Pro Ile Gln Arg Thr Ile Lys Pro Asp
            130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
            195                 200                 205

Arg Ile Thr Gly Tyr Ile Ile Lys Tyr Glu Lys Pro Gly Ser Pro Pro
        210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
            245                 250                 255

Lys Asn Asn Gln Lys Ser Glu Pro Leu Ile Gly Arg Lys Lys Thr
            260                 265                 270
```

(2) INFORMATION FOR SEQ ID NO:15:

(i) SEQUENCE CHARACTERISTICS:
        (A) LENGTH: 32
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: sequence of a part (1829-1860) of Heparin binding site of human plasma fibronectin (xi) SEQUENCE DESCRIPTION: SEQ ID NO:15:

```
Arg Pro Arg Pro Gly Val Thr Glu Ala Thr Ile Thr Gly Leu Glu Pro
1               5                   10                  15

Gly Thr Glu Tyr Thr Ile Tyr Val Ile Ala Leu Lys Asn Asn Gln Lys
                20                  25                  30
```

PEPTIDES DERIVED FROM THE HEPARIN BINDING DOMAIN OF FIBRONECTIN

FIELD OF THE INVENTION

This invention relates to a biological active peptide having cell adhesion inhibition activity.

BACKGROUND OF THE INVENTION

Many attempts have been done to establish a therapy for cancer, and such attempts have shown some advantageous therapeutic effects on several cancers. However, a method preventing cancer metastasis has not been established as yet.

Surgical therapy, radiotherapy and chemotherapy can be listed as a major method for therapy when one is diagnosed as getting cancer. When a patient shows clear abnormal symptom, most cancer probably becomes progressive and it is difficult to cure it. We can strongly believe that such difficulties is due to cancer metastasis and growing. Consequently, patient's condition after being cured mainly depends on the degree of cancer metastasis (Welch et al., Intern. J. Cancer, 43, 449, 1989). It is extremely difficult to cure cancer completely so long as such a cancer metastasis and growing are not suppressed. For example, in the case that stomach cancer becomes progressive, it is often that the cancer has already metastasized to lymph node, liver, lung and so forth. Such a phenomenon is occurred in breast cancer, it is reported that progressive cancer has metastasized to lymph node, which is adjacent to it, as well as bone marrow and lungs. Particularly, in regard to the epithelial cancer, the patient's condition after being cured depends on the degree of metastasis of cancer to lymph node (Shigeru Tsukakoshi, chemistry to cure cancer, Japan pharmaceutical society Pharmacia Review, No. 6).

Due to the above reasons, many attempts to elucidate detailed mechanism of cancer metastasis and apply its mechanism to therapy have done.

Cancer metastasis is constituted a complicated process in which cancerous cells departure from primary spot, infiltrate to peripheral tissues and grow in that metastasized tissues. This process is influenced by both factors of cancerous cell and host cell. In the former, the primary spot suffers from continuous gene alteration and consists of an uniformity cell mass showing various cytomorphosis, such as proliferation potency, drug sensitiveness, immunogenicity, configuration, etc. As factors of cancerous cell, metastasis ability, infiltration ability to periphery tissues, production of self growth factors from metastatic cancerous cell, and the like influence cancer metastasis. As factors of host cell, physical and anatomical condition in the blood, defense mechanism of immunocompetent cell, adhesion interaction between endothelial cell and blood platelet, growth factors from periphery metastasized tissues, and the like influence cancer metastasis.

It seems that on the serial process for cancer metastasis, expression and regulation of metastatic properties of cancerous cell is influenced by the interaction between cancerous cell and normal host cell, the interaction of cancerous cells with each together, and the interaction between cancerous cell and various biological components such as cell external matrix. Adhesion between cancerous cells with each together or between cancerous cell and normal cell is mediated by a cell adhesion molecule expressed on cell surface, and, as such a cell adhesion molecule, cadherin molecular group (Masatoshi Takeichi, molecular basis for tissue construction—role of cadherin for cell recognition—biochemistry, 59, 1, 1987), immune globulin molecular group, secretin molecular group (Springer, T. A., Nature, 346, 425, 1990) and so forth are known. On the other hand, adhesion molecule on cell surface including integulin molecular group contributes adhesion between cancerous cell and external matrix including glycoprotein such as fibronectin, laminin and collagen, and proteoglycan being bound with heparan sulfate, chondroitin sulfate etc.

Recently, it was made clear that cell external matrix molecule such as fibronectin or laminin strongly participated in cancer metastasis. It is shown that, after cell suffers from malignant transformation by oncogenic virus or chemical carcinogenesis agent etc., synthesis or accumulation into cell external of cell external matrix molecule, especially fibronectin, is decreased (Yamada, K. M. and Olden, K., Nature, 275, 179, 1978), expression of integrin molecule is decreased, and its adhesion ability to fibronectin is decreased (Plantefaber, L. C. and Hynes, R. O., Cell, 56, 281, 1989). It is also reported that fibronectin and laminin promote adhesion and metakinesis ability of cancerous cell (McCarthy, J. B., J. Cell Biol., 98, 1474, 1984).

Fibronectin and laminin molecule have domain configuration and let lots of functions disperse in the molecule. Configuration is made clear by biochemical or genetic engineering procedure, and existence of cell adhesion portion and receptor for it are discovered. RGD sequence in cell binding domain of fibronectin is cell recognition sequence (Pierschbacher, M. D., Nature, 309, 30, 1984), and the sequence exists and functions in lots of cell adhesion related molecules, and the receptor for the sequence is identified as alpha 5 beta 1 integrin receptor (Pytela, R., Cell, 40, 191, 1985).

Adhesion interaction between cell adhesion molecule and cell has been made clear, and recently application of cell adhesion peptide to inhibit cancer metastasis has been attempted. Humphries et al. show that GRGDS peptide as an adhesion signal of fibronectin inhibits experimental metastasis of melanoma cell to lung (Humphries, M. J., Science, 233, 467, 1986).

However, there are lots of problems to be solved in which clearance rate of the peptide in the blood after administration is fast and the peptide tends to be easily digested by enzyme for applying the peptide as a medicine (Saiki, I. et al., Jpn. J. Cancer Res., 84, 558, 1993).

Exploration of cancer metastasis inhibition materials as mentioned above is necessary to cure cancer completely. However, no substance being excellent medicine for cancer has obtained up to now.

SUMMARY OF THE INVENTION

In the light of the foregoing demand, the present invention was made. The purpose of the present invention is to provide a new peptide having cell adhesion inhibition activity.

The inventors have made an extensive study to resolve the above problems, and found a new peptide having cell adhesion inhibition activity, especially a peptide including the amino acids sequence described in the SEQ ID NO:13 of the sequence listing.

The present invention is a peptide which has the number of amino acids of 30 or less, comprises the amino acid sequence described as the SEQ ID NO:13 in the sequence listing and has cell adhesion inhibition activity.

The present invention is also a peptide which comprises the amino acid sequence described as the SEQ ID NO:13 in the sequence listing and has cell adhesion inhibition activity and which is characterized by having the number of amino acids of 13–30.

Further, the present invention is a peptide which has the number of amino acids of 30 or less, comprises the amino acid sequence described as the SEQ ID NO:8 in the sequence listing and has cell adhesion inhibition activity.

Furthermore, the present invention is a peptide which has the number of amino acids of 30 or less, comprises the amino acid sequence described as the SEQ ID NO:11 in the sequence listing and has cell adhesion inhibition activity.

Still further, the present invention is a peptide which has the number of amino acids of 30 or less, comprises the amino acid sequence described as the SEQ ID NO:12 in the sequence listing and has cell adhesion inhibition activity.

The present invention is also a peptide derived from the above-mentioned peptides by insertion, deletion or substitution of one or several amino acids and has the cell adhesion inhibition activity.

In addition, the present invention is a cancer metastasis inhibitor comprising at least one peptide of the above-mentioned peptides.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the present invention, are given by way of illustration only, since various changes and modifications within the spirit and scope of the present invention will be apparent to those skilled in the art from this detailed description.

BRIEF DESCRIPTION OF THE DRAWINGS

FIG. 2 shows the relationship among each peptide (sequence ID No.15) used in Experiment 2.

DESCRIPTION OF THE PREFERRED EMBODIMENTS

Figure 1:
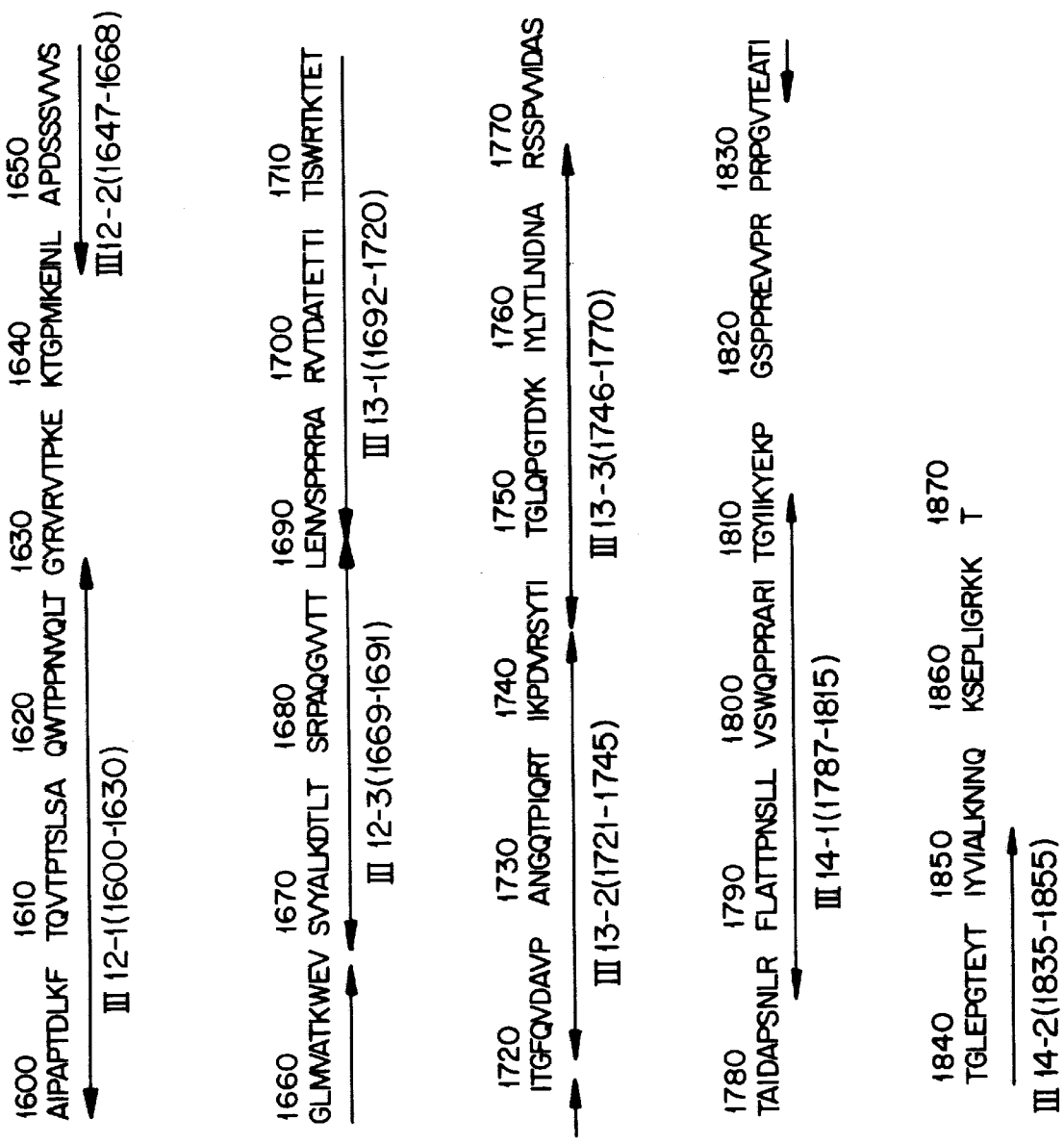
FIG. 1 shows the sequence of Hep 2 (sequence ID No.14) fragment and a position thereon of each peptide used in Experiment 1. The numeral of amino acid shows its position on fibronectin.

The present invention is a new peptide having cell adhesion inhibition activity, and is characterized by including the amino acids sequence described in the SEQ ID NO:13 of the sequence listing. The peptide of the present invention is very short length peptide and, therefore, the peptide can be synthesized easily and provides strong cell adhesion inhibition activity without any denaturation treatment such as urea treatment.

The amino acids sequence of the peptide of the present invention, i.e. amino acids sequence described in the SEQ ID NO:13 of the sequence listing, is the same as the amino acids sequence of 1848–1855 portion of fibronectin.

It is reported that fibronectin has cell adhesion activity (Hynes, R. O. et al., J. Cell Biol., 95, 369–377, 1982). On the other hand, it is reported that 30 kDa fragment (Hep 2) derived from Hep 2 domain of fibronectin becomes to have strong cell adhesion inhibition activity after being denaturated by urea (Fukai, F. et al., Biochemica. Biophys. Res. Commun., 220, 394, 1996). However, it did not suggest or indicate that which amino acid sequence contributes the cell adhesion inhibition activity of Hep 2. Furthermore, Hep 2 consists of 271 amino acids. As a result, the attempt in which Hep 2 itself will be used as a medicine is not desirable because Hep 2 has a high molecular weight and includes non related sequence of cell adhesion inhibition activity. The synthesis and preparation of Hep 2 is difficult because of its high molecular weight, and it is likely that an amino acid sequence which does not contribute the cell adhesion inhibition activity of Hep 2 shows undesirable biological activity. Also it is very complicated procedure to remove urea after being treated with urea and denaturated. Furthermore, high molecular weight molecules can be easily digested in vivo. Due to the above reasons, it is difficult that Hep 2 denatured with urea it self is used as a medicine.

The peptide having cell adhesion inhibition activity of the present invention is characterized in that it includes the sequence described as the SEQ ID NO:13 of the sequence listing, and the sequence has a sequence which is absolutely different from the reported peptide sequences having RGD sequence (Humphries, M. J. et al., Science, 233, 467, 1986, Komazawa, H. et al., Biol. Pharm. Bull., 16, 10, 997, 1993). Thus, the cell adhesion inhibition activity of the peptide of the present invention seems not to be mediated by the receptor which is effected by the RGD peptide (Pytela, R. et al., Cell, 48, 549, 1987). Therefore, the peptide of the present invention is a novel peptide sequence having cell adhesion inhibition activity. Furthermore, the cell adhesion inhibition activity is confirmed to be several times stronger than that of the RGD peptide (see the following Examples).

The amino acids sequence described as the SEQ ID NO:13 of the sequence listing is a common sequence among the peptides which shows the cell adhesion inhibition activity found by the inventors. Therefore, the peptide having cell adhesion inhibition activity of the present invention is characterized in that it includes the amino acids sequence described as the SEQ ID NO:13 of the sequence listing. If a peptide has the amino acids sequence described as the SEQ ID NO:13 of the sequence listing in an integral times repeated configuration, the peptide is expected to have more stronger cell adhesion inhibition activity. Such a peptide is also covered with the present invention. The peptide of the present invention includes any amino acid sequences as long as it includes the amino acid sequence described as the SEQ ID NO:13 of the sequence listing. Such a peptide is also covered with the present invention. The size (the number of amino acids) of the peptide of the present invention is preferably 30 or less amino acids, more preferably 13–30 amino acids, in the light of synthesis efficiency, handling, stability and so forth.

One or several amino acids of the peptide of the present invention may be inserted, deleted or substituted as long as it has the cell adhesion inhibition activity according to the present invention. Such a peptide is covered with the present invention. The insertion, deletion or substitution of one or several amino acids can be made by using a conventional methods such as site-directed mutagenesis.

Also, the derivative of the peptide of the present invention which includes the amino acids sequence described as the SEQ ID NO:13 of the sequence listing is expected to have the same or similar effect as the above-mentioned cell adhesion inhibitor peptide, and such a peptide (derivative) is also covered with the present invention. As a method for modifying peptide, for example, modification by using polymer such as polyethylene glycol (PEG) or circularization of linear peptide (Saiki, I. et al., Jpn. J. Cancer Res., 84, 558, 1993) can be listed, but it is not limited to those methods. As long as the cell adhesion inhibition activity is not missed, the peptide of the present invention may be modified by modifying a side chain of the amino acid constituting the peptide with utilization of ester bond, ether bond and so forth. Such a peptide is also covered with the present invention.

The peptide of the present invention having the amino acid sequence described as the SEQ ID NO:13 of the sequence listing is thought to be highly hydrophobic base on its amino acid sequence. The peptide of the present invention may be modified by hydrophilic amino acid, a hydrophilic group (such as ethylene glycol and polyethylene glycol) and so forth to induce hydrophilic property of the peptide. Such a modified peptide is also covered with the present invention.

The cell adhesion inhibition peptide of the present invention is useful for investigation and care of the various kinds of disease in which cell adhesion participates. As such a disease, cancer, rheumatism, asthma, allergic disease, thrombosis, rejection against transplantation, healing of wound, inflammation, immunological inflammation containing enteritis nephrocalcinosis (such as colitis ulcerosa), and autoimmune disease can be listed, but it is not limited to these diseases.

The cell adhesion inhibition peptide of the present invention can be administrated by intravenous administration, focus administration to an affected part, oral administration and so forth. Also, additives such as stabilizer and solubilizer can be added on administration if needed.

The cell adhesion inhibition peptide of the present invention can be synthesized by, for example, chemical synthesis such as solid phase chemical synthesis, or gene technology using gene recombinant procedure in which a DNA sequence coding amino acid sequence described as the SEQ ID NO:13 is inserted into a plasmid vector, microorganism such as $E.\ coli$ is transformed with the inserted vector and the peptide is produced. Chemical synthesis is generally done by using a commercialized peptide synthesizer. In the synthesis method using gene recombinant technology, for example, a gene coding the cell adhesion inhibition peptide is synthesized by using DNA synthesizer, the gene is inserted into a known plasmid vector, the resultant recombinant vector is transformed into a host microorganism to form a recombinant and thus the cell adhesion inhibition peptide is produced. Any expression vector for producing a protein can be used as a plasmid vector used in the synthesis method. Further, the host is not limited to microorganism and eucaryotic cells such as COS cell can be used.

The present invention will be described in detail based on the following working examples. However, the scope of the present invention is not limited by these examples.

Experiment 1: Cell Adhesion Inhibition Activity of a Synthetic Peptide (a System in Which Cell Suspension Includes a Synthetic Peptide)

The peptide (peptide III 14-2) consisting of the amino acid sequence described as the SEQ ID NO:8 in the sequence listing was used in Examples 1–3.

Hep 2 fragment treated without urea (Hep 2) was used in Comparative Example 1, and Hep 2 fragment treated with urea (Hep 2-urea) was used in Comparative Example 2. Hep 2 fragment was prepared by a method according to the method of Fukai et al. (Biochem. Biophys. Res. Commun., 220, 394–398, 1996). Hep 2 fragment treated without urea was prepared according to the above method and dissolved in phosphate buffer. Urea treated Hep 2 fragment was prepared by treating with urea according to the method of Fukai et al. mentioned above and thereafter dialyzed against phosphate buffer.

The GRGDSP peptide of cell adhesion domain (describes as the SEQ ID NO:9 of the sequence listing), which has been known as a cell adhesion inhibition peptide, was used in Comparative Example 3. The GRGDSP peptide (purchased from IWAKI GLASS, Japan) was dissolved in phosphate buffer.

The peptides consisting of the amino acid sequence described as the SEQ ID NO:1 (peptide III 12-1), the SEQ ID NO:2 (peptide III 12-2), the SEQ ID NO:3 (peptide III 12-3), the SEQ ID NO:4 (peptide III 13-1), the SEQ ID NO:5 (peptide III 13-2), the SEQ ID NO:6 (peptide III 13-3) and the SEQ ID NO:7 (peptide III 14-1) were used in Comparative Examples 4–9, respectively.

All of the peptides which were used in Examples 1–3 and Comparative Examples 4–9 were synthesized by applying SAWADY TECHNOLOGY CO., LTD., Tokyo, Japan for synthesis and by using a peptide synthesizer (Multiple Peptide Synthesizer (SYRO II), MultiSynTec GmbH). Further, the sequences of the resultant synthesized peptides were confirmed by using a peptide sequencer (Model 476A, Applied Biosystems).

Each of the synthetic peptides used herein is a peptide corresponding to a part of the sequence of Hep 2 fragment which is derived from Heparin binding domain 2 of fibronectin molecule. Each peptide sequence and Hep 2 sequence as well as the relationship between them are showed in FIG. 1.

The above synthetic peptides were used in this experiment after being dissolved in dimethyl sulfoxide (DMSO: Wako Jyunyaku Co.). To adjust a condition of each experiment to the same, DMSO was added into phosphate buffers containing urea-non-treated Hep 2 fragment, urea-treated Hep 2 fragment, GRGDSP peptide and phosphate buffer itself as a control, respectively. The concentration of DMSO of each experiment was adjusted to 0.2% of final concentration. Inhibition activity against cell adhesion was evaluated according to the method of Fukai et al. (Biochem. Biophys. Res. Commun., 220, 394–398, 1996). In other words, the inhibition activity against cell adhesion of A375 melanoma cell to a plate was measured under the condition with or without the above various synthetic peptides. A375 melanoma cell (American Type Culture Collection: ATCC) was suspended in Dulbecco's modified eagle medium (DMEM: Gibuco Co.) including 0.1% Ovalbumin (Wako Jyunyaku Co.) to be a concentration of $2 \times 10^5$ cells/ml. Before preparing cell suspension, a plate was coated with fibronectin according to the method of Miekka et al. Specifically, phosphate buffer containing 10 µg/ml of fibronectin (FN) was prepared and 100 µl of the resultant phosphate buffer containing fibronectin was added into each well of a 96-well plate and then the plate was incubated at 37° C., 5% $CO_2$ concentration for 60 minutes before being washed with phosphate buffer three times. Fibronectin (FN) was purified according to the method of Miekka et al. (Thromb. Res., 27, 1–14, 1982). One hundred (100) µl of the above cell suspension was added into each well of the plate and the plate was incubated at 37° C., 5% $CO_2$ concentration for 60 minutes (Control was without any synthetic peptide). After fixing cells in each well with 5% of formaldehyde (Wako Jyunyaku Co.), non adhesion cells were removed and calls in five areas selected at random in each well were counted by the use of a microscope.

The addition of Hep 2 fragment and each peptide was carried out by the step in which a solution containing Hep 2 fragment or each peptides dissolved with high concentration was added to the cell suspension to obtain the final concentration of Hep 2 fragment or each peptides shown in Table 1.

The results are shown in Table 1. Table 1 shows that the Hep 2 fragment without urea treatment does not have cell adhesion inhibition activity at all, but after being treated with urea the Hep 2 fragment (Hep 2-urea) has the activity. The peptide III 14-2 has the highest cell adhesion inhibition activity and the activity depends on the concentration of the peptide.

TABLE 1

Cell adhesion inhibition activity of synthetic peptides

| Fragment or synthetic peptide | Concentration ($\mu$g/ml) | Cell adhesion inhibition activity*1) (%) |
|---|---|---|
| Control | — | 0 |
| Comparative Example 1(Hep2) | 200 | 0 |
| Comparative Example 2(Hep2-urea) | 50 | 51 |
| Comparative Example 3(GRGDSP) | 200 | 35 |
| Comparative Example 4(III 12-1) | 200 | 11 |
| Comparative Example 5(III 12-2) | 200 | 13 |
| Comparative Example 6(III 12-3) | 200 | 7 |
| Comparative Example 7(III 13-1) | 200 | 4 |
| Comparative Example 8(III 13-2) | 200 | 11 |
| Comparative Example 9(III 13-3) | 200 | 9 |
| Comparative Example 10(III 14-1) | 200 | 11 |
| Example 1 (III 14-2) | 200 | 71 |
| Example 2 (III 14-2) | 20 | 44 |
| Example 3 (III 14-2) | 2 | 20 |

*1) The cell adhesion inhibition activity is calculated by counting the number of adhesion cells of the control as 100%, obtaining a percentage of a number of adhesion cells of each of the examples and the comparative examples in which each fragment or peptide is used in comparison with the number of the control (100%), and subtracting the percentage thus obtained from 100.

Experiment 2: Cell Adhesion Inhibition Activity of a Synthetic Peptide (a System in Which a Plate is Coated With Fibronectin Solution Containing a Synthetic Peptide)

It is evaluated that which part of the sequence of the peptide III 14-2 contributes its cell adhesion inhibition activity.

The peptides consisting of the amino acid sequence described as the sequence ID NO: 8 (peptide III 14-2), the sequence ID NO: 10 (peptide III 14-2A), the sequence ID NO: 11 (peptide III 14-2B) and the sequence ID NO:12 (peptide III 14-2C) were used as the synthetic peptide.

The peptide III 12-2 used in Experiment 1 was used as a control.

All of the peptides which were used in this experiment were synthesized by applying SAWADY TECHNOLOGY CO., LTD., Tokyo, Japan for synthesis and by using a peptide syntehsizer (Multiple Peptide Synthesizer (SYRO II), MultiSynTec GmbH). Further, the sequences of the resultant synthesized peptides were confirmed by using a peptide sequencer (Model 476A, Applied Biosystems).

Each of the synthetic peptides used herein was the peptide corresponding to a part of the sequence of Hep 2 fragment which was derived from the heparin binding domain 2 of fibronectin molecule. The relationship among sequences of the peptides is showed in FIG. 2.

All of the synthetic peptides used herein were peptides modified with maleimide-activated Keyhole Limpet Hemocyanine (KLH: PIERCE Co., USA) in order to improve their solubility into phosphate buffer and to coat them to a plate completely (this modification does not influence cell adhesion inhibition activity at all).

Figure 3:
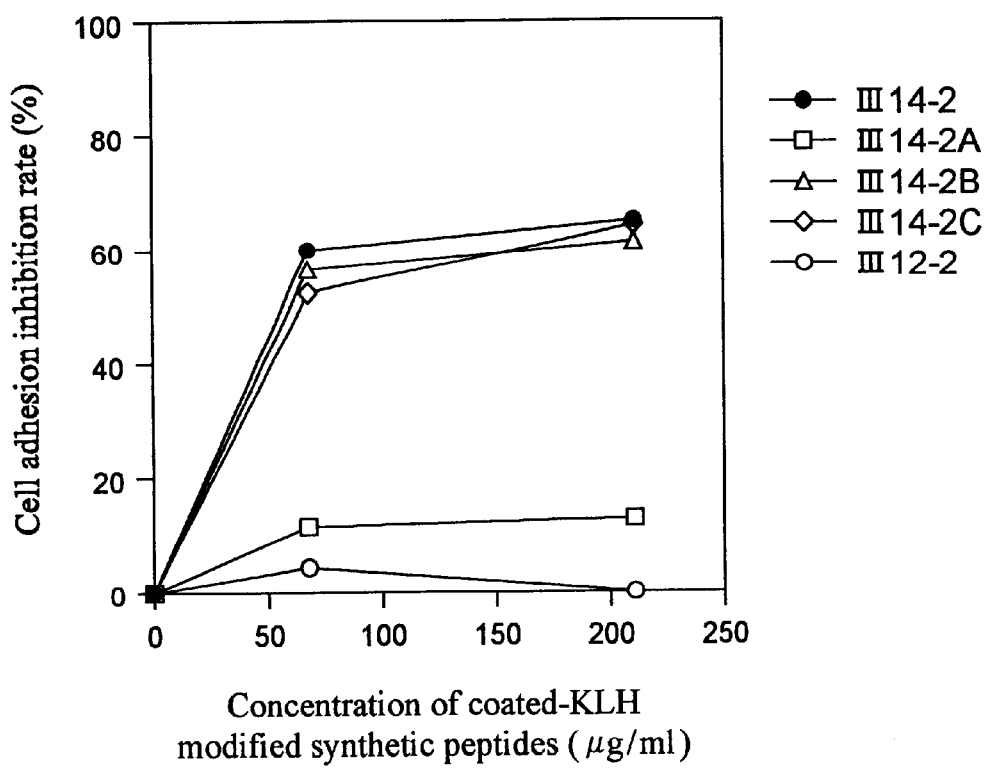
FIG. 3 shows the result of the evaluation of cell adhesion inhibition activity of each KLH modified synthetic peptide.

The above various KLH modified synthetic peptides were added to a solution containing fibronectin to obtain a given concentration, then the procedure of Experiment 1 were repeated with the exception that the resultant solution were added into 96-well plate to coat it. The experiment without any synthetic peptide is a control (the concentration of a peptide was 0 $\mu$g/m 1). The results are shown in FIG. 3. FIG. 3 shows that, among three peptides containing a part of the peptide III 14-2 (peptides III 14-2A, III 14-2B and III 14-2C), the peptide III 14-2A has very little cell adhesion inhibition activity, while the other two peptides (peptides III 14-2B and III 14-2C) have the same strong cell adhesion inhibition activity as that of the peptide III 14-2. These results indicate that the common amino acid sequence among these three peptides, peptide III 14-2, peptide III 14-2B and peptide 14-2C (amino acid sequence of YTIYVIAL described as the sequence ID No: 13 of the sequence listing) has cell adhesion inhibition activity.

The peptide of the present invention has cell adhesion inhibition activity and, therefore, the peptide can be applied to investigation and therapy of various kind of disease in which cell adhesion participates in. Further, because the peptide of the present invention has cell adhesion inhibition activity the same as or more stronger than that of known cell adhesion inhibition materials and has short length, the synthesis and handling of the peptide of the present invention are easy. Furthermore, the peptide of the present invention is useful as an agent inhibiting cancer metastasis because the peptide has inhibition activity against cancerous cell adhesion.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No.8-248247 (248247/1996) filed on Sep. 19, 1996 is hereby incorporated by reference.

What is claimed is:

1. A peptide consisting of an amino acid sequence described as sequence ID No: 13 in the sequence listing.

2. A peptide consisting of an amino acid sequence described as sequence ID No. 8 in the sequence listing.

3. A peptide consisting of an amino acid sequence described as sequence ID No: 11 in the sequence listing.

4. A peptide consisting of an amino acid sequence described as sequence ID No: 12 in the sequence listing.

* * * * *